(12) United States Patent
Huang et al.

(10) Patent No.: US 10,168,273 B1
(45) Date of Patent: Jan. 1, 2019

(54) METHODS AND APPARATUS FOR POLARIZING RETICLE INSPECTION

(71) Applicant: KLA-Tencor Corporation, Milpitas, CA (US)

(72) Inventors: Haifeng Huang, Livermore, CA (US); Rui-Fang Shi, Cupertino, CA (US); Damon F. Kvamme, Los Gatos, CA (US); Amrish Kelkar, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 15/795,089

(22) Filed: Oct. 26, 2017

Related U.S. Application Data (60) Provisional application No. 62/528,038, filed on Jul. 1, 2017.

(51) Int. Cl.
  *G01J 4/00* (2006.01)
  *G01N 21/21* (2006.01)
  *G01N 21/956* (2006.01)

(52) U.S. Cl.
  CPC ........... *G01N 21/21* (2013.01); *G01N 21/956* (2013.01); *G01N 2021/95676* (2013.01); *G01N 2201/0683* (2013.01)

(58) Field of Classification Search
  CPC ................. G01N 21/211; G01N 21/21; G01N 2021/213; G01J 4/00; G01B 11/0641
  USPC ......................................................... 356/369
  See application file for complete search history.

(56) References Cited

U.S. PATENT DOCUMENTS

| | | | |
|---|---|---|---|
| 6,211,957 B1 | 4/2001 | Erdogan et al. | |
| 6,373,614 B1 | 4/2002 | Miller | |
| 7,345,740 B2 | 3/2008 | Wagner et al. | |
| 2004/0207843 A1* | 10/2004 | Westbrook | G01J 4/00 356/364 |
| 2006/0092398 A1 | 5/2006 | McCarthy | |

(Continued)

OTHER PUBLICATIONS

Goldstein, Dennis, "Polarized Light", "Polarized Light", 2nd Ed., Revised and Expanded, by Dennis Goldstein, Marcel Dekker, Inc., New York 2003., 2003, 4 pages.

*Primary Examiner* — Md M Rahman
(74) *Attorney, Agent, or Firm* — Kwan & Olynick, LLP (57) ABSTRACT

Disclosed are methods and apparatus for measuring and controlling polarization for inspection of a semiconductor sample. The method includes (i) setting up an inspection system in a specific mode of operation, (ii) incrementing a first waveplate of the system through a plurality of rotations while keeping a second waveplate of the system static, (iii) measuring an intensity signal from non-patterned areas of the sample for each rotation of the first waveplate, (iv) incrementing the second waveplate through a plurality of rotations while keeping the first waveplate static (v) measuring an intensity signal from non-patterned areas of the sample for each rotation of the second waveplate, (vi) generating a model of a plurality of polarization and waveplate parameters for the system to simulate the intensity signals that were measured for each rotation of the first and/or second waveplate, and (vii) determining the polarization and waveplate parameters for the system based on the model and a polarization state on photomask plane based on the polarization and waveplate parameters.

20 Claims, 7 Drawing Sheets

(56) References Cited

U.S. PATENT DOCUMENTS

| | | | |
|---|---|---|---|
| 2006/0215157 A1* | 9/2006 | Westbrook | G01J 4/00 356/364 |
| 2014/0242880 A1* | 8/2014 | David | B24B 49/12 451/5 |
| 2015/0103348 A1* | 4/2015 | Zhao | G01N 21/9501 356/369 |
| 2017/0276613 A1* | 9/2017 | Liu | G01N 21/21 |
| 2018/0013988 A1* | 1/2018 | Kondo | H04N 9/07 |

* cited by examiner

METHODS AND APPARATUS FOR POLARIZING RETICLE INSPECTION

CROSS-REFERENCE TO RELATED APPLICATION

This application claims priority to U.S. Provisional Patent Application No. 62/528,038, filed 1 Jul. 2017, which application is incorporated herein by reference in its entirety for all purposes.

TECHNICAL FIELD OF THE INVENTION

The invention generally relates to the field of reticle or photomask inspection systems. More particularly the present invention relates to techniques for management of polarization for defect detection.

BACKGROUND

Generally, the industry of semiconductor manufacturing involves highly complex techniques for fabricating integrated circuits (IC) using semiconductor materials which are layered and patterned onto a substrate, such as silicon. Due to the large scale of circuit integration and the decreasing size of IC features in semiconductor devices, fabricated devices have become increasingly sensitive to defects. That is, defects which cause faults in devices are becoming increasingly smaller. Devices need to be generally fault free prior to shipment to the end users or customers.

Various inspection systems are used within the semiconductor industry to detect defects on a semiconductor reticle or wafer. However, there is a continuing demand for improved semiconductor reticle and wafer inspection systems and techniques.

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

An inspection system for controlling and measuring polarization for inspection of a photomask sample is disclosed. The system generally includes an illumination optics subsystem for generating and directing illumination light towards a sample, wherein the illumination optics subsystem includes two or more illumination polarization components for controlling the polarization state of the illumination light. The system also includes a collection optics subsystem for collecting output light from non-patterned areas of the sample in response to the illumination light. The collection optics subsystem comprises at least a first and second collection polarization component for measuring polarization state of the illumination light at or near the sample and a sensor for detecting the output light after the polarization state is adjusted by the first and second collection polarization components. The system further comprises a controller that is configured to perform the following operations: (i) setting up the system in a specific mode of operation, (ii) incrementing the first collection polarization component through a plurality of rotations while keeping the second collection polarization component static, (iii) measuring an intensity signal by the sensor for each rotation of the first collection polarization component, (iv) incrementing the second collection polarization component through a plurality of rotations while keeping the first collection polarization component static, (v) measuring an intensity signal by the sensor for each rotation of the second collection polarization component, (vi) generating a model of a plurality of polarization state and polarization component parameters for the system to simulate the intensity signals that were measured for each rotation of the first and/or second collection polarization component, and (vii) determining the polarization state and polarization component parameters for the system based on the model. In one aspect, the model is based on Jones calculus and uses a nonlinear least squares fit process to determine the polarization state and polarization component parameters.

In a specific implementation, the illumination optics subsystem includes one or more light sources for generating illumination light that is transmitted through the sample in a transmitted light (TL) mode. In one implementation, the at least first and second collection polarization components comprise a first and second waveplate, and the system is set up in the TL mode. In one aspect, a model is first generated based on Jones calculus and used to determine a retardance value for the first waveplate and the polarization state between the first waveplate and the second waveplate based on measuring for each rotation of the first waveplate and a model is next used to determine a retardance of the second waveplate and the polarization state at or near the sample based on measuring for each rotation of such second waveplate and the determined retardance of the first waveplate and its static rotation position. In a further aspect, the first waveplate is a rotatable ¼ waveplate and the second waveplate is a rotatable ⅜ waveplate, and the ⅜ waveplate is positioned to receive the output light from the non-patterned areas of the sample, after which the ¼ waveplate receives the output light from the ⅜ waveplate. Other waveplate combinations having a retardance sum equal to or greater than a half wave can be used.

In yet a further implementation aspect, the illumination optics subsystem includes one or more light sources for generating illumination light that is reflected from the sample in a reflected light (RL) mode, and the collection optics subsystem includes a polarizing beam splitter (PBS) for receiving the output light from the ¼ waveplate and transmitting only a y-polarization component of the output light towards the sensor, and the PBS is arranged and configured to reflect only an x-polarization component of illumination light in RL mode towards the sample. In a specific aspect, the polarization state of the illumination light at or near the sample is determined as a function of field position.

In another embodiment, the first and second waveplates are the same as at least some of the illumination polarization components, and the controller is further configured for setting up the system in RL mode and performing the following operations: (i) incrementing the first waveplate through a plurality of rotations while keeping the second waveplate static, (ii) measuring an intensity signal by the sensor for each rotation of the first waveplate, (iii) generating a model based on Jones calculus and of a plurality of polarization and waveplate parameters, including the retardance of the first and second waveplates, for the system to simulate the intensity signals that were measured for each rotation of the first waveplate, and (iv) determining illumination polarization state at or near the sample based on the determined retardance of the first and second waveplates and the rotation of the first waveplate. In a further aspect, the controller is configured for, modeling a sinusoidal behavior of the retardance of the second waveplate as a function of rotation and separating a real retardance of the second waveplate from a retardance of an objective of the system based on such modelled sinusoidal behavior.

In an alternative embodiment, the at least first and second collection polarization component comprise a plurality of waveplates having a retardance sum equal to or greater than a half wave. In another example, the collection optics subsystem includes multiple detection planes for detecting output light, and the controller is further configured to model and determine the polarization state and polarization component parameters for measurements at the multiple detection planes and average the determined polarization state and polarization component parameters from such multiple detection planes. In another aspect, the controller is further configured for simulating a plurality of polarization states at or near the sample based on the determined polarization state and polarization component parameters and selecting a rotation for the first and second collection polarization components to result in a particular orientation of linear polarization at the sample.

In another embodiment, the invention pertains to a method of controlling polarization for inspection of a semiconductor sample. The method includes (i) setting up an inspection system in a specific mode of operation, (ii) incrementing a first polarization component of the system through a plurality of rotations while keeping a second polarization component of the system static, (iii) measuring an intensity signal from non-patterned areas of the sample for each rotation of the first polarization component, (iv) incrementing the second polarization component through a plurality of rotations while keeping the first polarization component static (v) measuring an intensity signal from non-patterned areas of the sample for each rotation of the second polarization component, (vi) generating a model of a plurality of polarization state and polarization component parameters for the system to simulate the intensity signals that were measured for each rotation of the first and/or second polarization component, and (vii) determining the polarization state and polarization component parameters for the system based on the model. In further aspect, the method includes operations that are similar to one or more of the controller operations outlined above.

These and other aspects of the invention are described further below with reference to the figures.

DETAILED DESCRIPTION OF EXAMPLE EMBODIMENTS

In the following description, numerous specific details are set forth in order to provide a thorough understanding of the present invention. The present invention may be practiced without some or all of these specific details. In other instances, well known component or process operations have not been described in detail to not unnecessarily obscure the present invention. While the invention will be described in conjunction with these specific embodiments, it will be understood that it is not intended to limit the invention to these embodiments.

Certain inspection system embodiments are described herein as being configured for inspecting semiconductor structures, specifically photolithography reticles. Other types of structures, such as semiconductor wafers, solar panel structures, optical disks, etc., may also be inspected or imaged using the inspection apparatus of the present invention.

Certain imaging inspection systems include configurable polarization control and measurements systems. For instance, polarization state control of 193 nm illumination light is one of the many useful tuning knobs that are available in RAPID 6xx photomask defect inspection tools by KLA-Tencor from Milpitas, Calif. Since the inspection sensitivity of certain types of reticle defects strongly depend on the polarization state of 193 nm illumination light, a polarization feature and its control has become increasingly important for improving inspection results for reticle defect detection and maintaining tool-to-tool matching. The importance of a polarization management system is especially evident for extreme ultra violet (EUV) photomasks on which the pattern sizes are typically much smaller than the wavelengths used in such systems, resulting in strong dependence of both the base pattern contrast and defect signal strength on the polarization state of the light.

Certain embodiments of the present invention provide polarization systems and techniques for measuring and controlling, both in situ and quantitatively, the polarization state of illumination light (e.g., 193 nm) on the photomask plane by use of certain inspection systems' available waveplate (WP, retarder) cascade module, which contains multiple waveplates. The techniques described herein include both polarization measurement and control and do not require an additional hardware change/replacement for systems having multiple waveplates, such as on the RAPID 6xx tool of KLA-Tencor. Certain techniques described herein provide detailed information of the illumination light polarization state, for example, in both inspection simulation and inspection data modeling, which also facilitates the quantitative assessment of inspection tool performance.

Certain techniques described herein provide measurements of the polarization states of illumination light (e.g., 193 nm) on the mask plane under both transmitted light (TL) and reflected light (RL). The polarization state is described by two parameters ellipticity and ellipse orientation angle. As a byproduct, these techniques can also provide accurate measurements of the phase retardance and slow axis orientation angles of waveplates. Based on these results, various polarization states, e.g. linear polarization with a specific orientation angle, can be predicted and produced by adjusting the orientation angles of the waveplates in the cascade design, by way of example.

Certain embodiments of the present invention provide compensation for system errors in a multiple-waveplate cascade design so as to achieve accurate polarization states, e.g. accurate circular polarization. In addition to compensating for imperfections in the waveplates (e.g., have retardance errors), compensation for other system errors can also be applied. For instance, certain techniques described herein can also provide measurements and compensation for the small residual birefringence of optics and finite extinction ratio of the polarizing beam splitter (PBS) in the image path in KLA-Tencor RAPID 6xx tools or the like.

Figure 1:
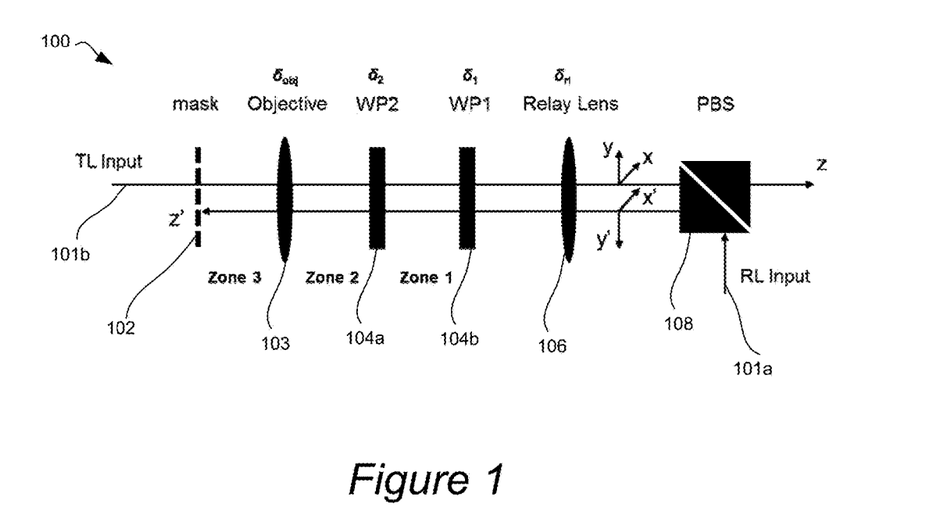
FIG. 1 is a diagrammatic representation of a multiple-waveplate cascade design for controlling and measuring polarization for both reflected and transmitted illumination modes in accordance with one embodiment of the present invention.

In certain embodiments, polarization may be measured and controlled for both reflected and transmitted illumination light although either mode may be utilized. FIG. 1 is a diagrammatic representation of a multiple-waveplate cascade design for controlling and measuring polarization for both reflected and transmitted illumination modes in accordance with one embodiment of the present invention. As shown, direction z corresponds to a direction in which the TL illumination beams are traveling. In this implementation, the illumination beams have a wavelength of about 193 nm. The illustrated xyz coordinate system is right-handed, and all the angles are defined herein in this xyz coordinate although other coordinate systems may be used.

In the illustrated example, the illumination light can take two forms: reflected light (RL) input 101a or transmitted light (TL) input 101b. In this example, the system 100 is configured to operate in either a TL or RL mode, but not at the same time. That is, RL or TL is performed one at a time.

The TL input 101b passes through the reticle (or other) sample 102, through objective 103, waveplates WP2 104a and WP1 104b, relay lens 106, and polarizing beam splitter (PBS) 108 towards a sensor (not shown). For the TL mode, the PBS is configured to pass y-polarization of such TL. In contrast, the PBS 108 is configured to reflect the x-polarization component of such TL light away from the sensor (not shown).

In contrast, RL input is coupled in through the PBS and travels against the z-axis, first passing the optics in a reversed sequence as compared to TL mode. More specifically, RL input 101a is reflected from PBS 108 at a right angle, through the relay lens 106, WP1 104b, WP2 104a, and objective lens 103, and reflected from the sample 102. The reflected output travels along the z-axis, in a same sequence as the TL mode, through objective 103, waveplates WP2 104a and WP1 104b, relay lens 106, and polarizer beam splitter 108 towards a sensor (not shown). For RL mode, the PBS 108 reflects the incident x-polarization RL towards the sample 102. Upon returning, the PBS 108 transmits the y-polarization component of the RL output towards the sensor (not shown), while reflecting x-polariza-tion away from the sensor (not shown). Thus, the PBS 108 is configured to pass only y-polarization output beams to the sensor.

A waveplate or retarder is an optical device that alters the polarization state of a light wave travelling through it. Two common types of waveplates are the half-wave plate, which rotates the polarization direction of linearly polarized light, and the quarter-wave plate, which converts linearly polarized light into circularly polarized light with correct relative orientation angle between linear polarization and the waveplate slow axis, and vice versa. A quarter-wave plate can be used to produce elliptical polarization as well.

Waveplates are constructed out of a birefringent material (such as quartz or mica), for which the index of refraction is different for different orientations of light passing through it. The behavior of a waveplate (that is, whether it is a half-wave plate, a quarter-wave plate, etc.) depends on the thickness of the crystal, the wavelength of light, and the variation of the index of refraction. By appropriate choice of the relationship between these parameters, it is possible to introduce a controlled phase shift between the two polarization components of a light wave, thereby altering its polarization A waveplate works by shifting the phase between two perpendicular polarization components of the light wave. A typical waveplate is simply a birefringent crystal with a carefully chosen orientation and thickness. The crystal is cut into a plate, with the orientation of the cut chosen so that the optic axis of the crystal is parallel to the surfaces of the plate. For a light wave normally incident upon the plate, the polarization component perpendicular to the optic axis travels through the crystal with a speed $v_o=c/n_o$, while the polarization component along the optic axis travels with a speed $v_e=c/n_e$ with different refractive index. This leads to a phase difference between the two components as they exit the crystal. When $n_e<n_o$, as in calcite, the optic axis is called the fast axis and the perpendicular axis is called the slow axis. For $n_e>n_o$ the situation is reversed. Although reference is made to a "slow axis" below, of course, these techniques can be used for the fast axis of the waveplate if a 90° shift is included.

In this example, WP1 is nominally a ¼ waveplate, while WP2 is nominally a ⅜ waveplate. WP1 is also referred to herein as WP1(λ/4), while WP2 is referred to as WP2(3λ/8). WP2(3λ/8) is closer to the objective than WP1(λ/4). Although the illustrated system 100 includes two waveplates, more than two waveplates may be implemented. Other waveplate combinations, with the combined waveplate phase retardance being equal to or greater than half wave, are also feasible designs of the waveplate cascade module.

The illustrated system 100 can have any number and type of parameters that can affect the polarization of light as it travels through the system, and these parameters can be measured using the techniques described herein. Parameter $\delta_{obj}$ is the effective retardance of the residual birefringence of the objective 103, which can come from $CaF_2$ parts, residual stress, and optical coatings of such component. $\delta_1$ and $\delta_2$ are the retardance parameters for WP1 and WP2, respectively. Their slow axis angles are $\theta_1$ and $\theta_2$, respectively. $\delta_{r1}$ is the residual birefringence of relay lens 106 (e.g., made of fused silica), which tends to be negligible.

Figure 2:
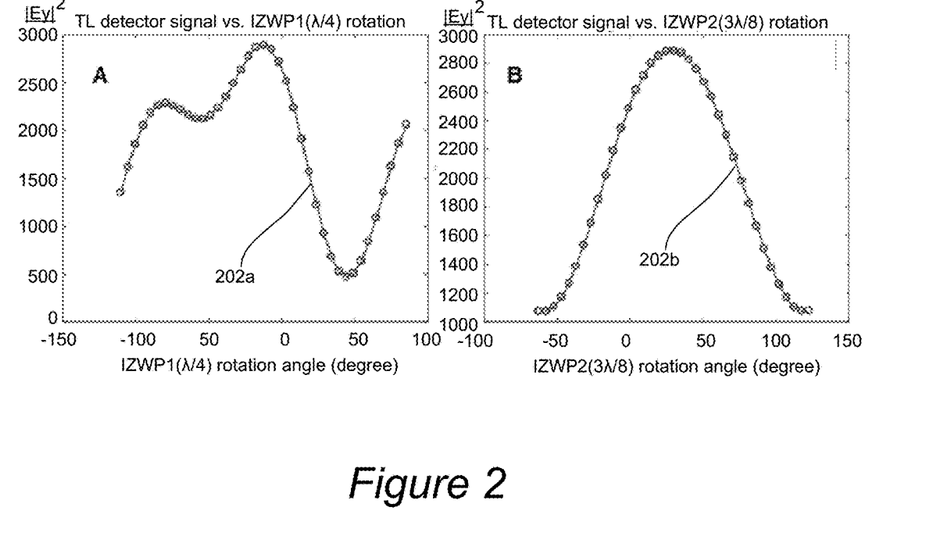
FIG. 2 show two graphs of TL (transmitted light) mode detected signal levels as a function of rotation of two different waveplates in accordance with one implementation of the present invention.

FIG. 2 show two graphs A and B of TL detected signal levels as a function of rotation of WP1(λ/4) and WP2(3λ/8), respectively. The vertical axis for graphs A and B corresponds to light intensity, which can be any units. The horizontal axis is the rotation angle of either WP1(λ/4) and WP2(3λ/8), in units of degrees. To obtain these plots, one waveplate, WP1(λ/4) or WP2(3λ/8), is held static while the other waveplate, WP2(3λ/8) or WP1(λ/4), is rotated step-by-step through a range of rotations angles, such as 0 to 180°. Each dot on each graph A and B is a detected light measurement.

After a number of measurements are obtained for each set of waveplate rotations, a model may then be used to fit the measurements to a curve, as illustrated by curves 202a and 202b, for example. This curve fitting process can then be used to obtain a retardance value for the different waveplates as further described below.

As background for generally characterizing light travelling through the system, the electric field convention is defined as:

$$e^{i(kz-\omega t+\varphi)} \quad \text{Equation 1}$$

with k being the wave vector; ω being the angular frequency of the light; and φ being the phase.

In Jones calculus, the polarization state of incident TL can be described by a Jones vector:

$$E^{in} = E_1 \begin{bmatrix} \cos(\beta) \\ \sin(\beta)e^{i\alpha} \end{bmatrix} \quad \text{Equation 2}$$

$E_1$ is amplitude, $\beta$ is an angle between 0 and $\pi/2$, and $\alpha$ is the phase difference between y- and x-components of the electric field. When describing polarization state, using the parameter pair ($\alpha$, $\beta$) in above Jones vector is equivalent to using another pair of commonly used quantities: ellipticity and ellipse orientation angle, which are related to $\alpha$ and $\beta$ through the following equations.

The parameter $S_3$ of normalized Stokes vector is $S_3=\sin(2\beta)\sin(\alpha)$, and the ellipticity $\rho$ is defined as $$\rho=S_3/(1+\sqrt{1-S_3^2}) \quad \text{Equation 3}$$

The ellipse orientation angle $\psi$ is defined in the range from −90° to 90° and is $$\tan(2\psi)=\tan(2\beta)\cos(\alpha) \quad \text{Equation 4}$$

The two waveplates can then be described by two Jones matrices, which are functions of the waveplate retardance parameters $\delta_1$ and $\delta_2$, respectively, and slow axis orientation angles $\theta_1$ and $\theta_2$ which are defined in xyz coordinates in FIG. 1, respectively.

$$J_1(\delta_1,\theta_1)$$

and $$J_2(\delta_2,\theta_2)$$

After TL transmits through WP2 and WP1, the output Jones vector is defined as the following equation:

$$E^{out}=J_1 \cdot J_2 \cdot E^{in} \quad \text{Equation 5}$$

The PBS transmits y-polarization TL, which is sensed by a sensor and can be modelled as:

$$|E_y^{out}|^2 = \begin{bmatrix} (-A_2\cos(\beta) + \sin(\beta)\cos(\alpha)A_0 + \sin(\beta)\sin(\alpha)A_1)^2 \\ +(A_3\cos(\beta) - \sin(\beta)\cos(\alpha)A_1 + \sin(\beta)\sin(\alpha)A_0)^2 \end{bmatrix} \quad \text{Equation 6}$$

with $A_0$, $A_1$, $A_2$, and $A_3$ defined as:

$$A_0 = \cos\left(\frac{\delta_2}{2}\right)\cos\left(\frac{\delta_1}{2}\right) - \sin\left(\frac{\delta_2}{2}\right)\sin\left(\frac{\delta_1}{2}\right)\cos(2(\theta_1-\theta_2))$$

$$A_1 = \cos\left(\frac{\delta_2}{2}\right)\sin\left(\frac{\delta_1}{2}\right)\cos(2\theta_1) + \sin\left(\frac{\delta_2}{2}\right)\cos\left(\frac{\delta_1}{2}\right)\cos(2\theta_2)$$

$$A_2 = \sin\left(\frac{\delta_2}{2}\right)\sin\left(\frac{\delta_1}{2}\right)\sin(2(\theta_1-\theta_2))$$

$$A_3 = \cos\left(\frac{\delta_2}{2}\right)\sin\left(\frac{\delta_1}{2}\right)\sin(2\theta_1) + \sin\left(\frac{\delta_2}{2}\right)\cos\left(\frac{\delta_1}{2}\right)\sin(2\theta_2)$$

Considering the finite extinction ratio e of the PBS, the light intensity after the PBS is:

$$F=\in \cdot E_1^2 + (1-\in)|E_y^{out}|^2 \quad \text{Equation 7}$$

It is this light intensity F that is captured by the sensor. Rotating either WP1 or WP2 will cause the above detected light intensity to change, and the changing of the light intensity as a function of waveplate rotation can be described by the above model. Fitting the recorded light intensity to the model F gives both the polarization states, i.e. $\beta$ and $\alpha$ polarization parameters, and waveplate parameters, such as slow angle orientations, and retardance parameters.

FIG. 2 shows one example of TL measurements obtained on one of the 6xx tools of KLA-Tencor. The fitted model function for these TL measurements is also plotted in FIG. 2. From the modelling and multiple measurements, $\delta_1$ and $\delta_2$ are determined to have values of 88.4° and 127.2°, respectively. These determined values are off by a few degrees from the ideal retardance values 90° and 135° of λ/4 and 3λ/8 waveplates, respectively. It is clear that with a single non-ideal λ/4 waveplate, one cannot realize accurate circular polarization state on the photomask plane. However, with a pair of non-ideal λ/4 and 3λ/8 waveplates, one can. With the data of WP1 rotation (WP2 static, FIG. 2A), at the WP1 position for circular polarization, the polarization state between WP1 and WP2 is determined to have an ellipticity of −0.346 and an orientation angle of 68.3°. With the data of WP2 rotation (WP1 static at designed position, FIG. 2B), at the WP2 position for circular polarization, the polarization state of Zone 2 in FIG. 1 is measured to have an ellipticity of 0.963.

A Levenberg-Marquardt (LM) nonlinear least squares fit algorithm may be used to obtain these parameter values and then to calculate polarization states. A curvature matrix may be generated by calculating all the necessary partial derivatives of the model (e.g. Equation 7) with regards to each fitted parameter such as polarization parameters $\alpha$ and $\beta$, and waveplate parameters (retardance and slow axis angles). The fitting programs may be fully optimized for the problem being solved. With the correct initial values of fitted parameters, the solution from the nonlinear least squares fitting is unique. This uniqueness is also true for the RL case, which is discussed below. Certain embodiments of the present invention provide a new method of using Jones calculus and nonlinear least squares fitting algorithms to measure polarization state and waveplate parameters at the same time.

In the RL case, 193 nm illumination light passes the optics twice. For the first pass, the light travels against the z-axis. The PBS 108 also only reflects the x polarization component of the RL input towards the sample. Thus, α and β for the RL input into the system are both zero. The coordinate x'y'z' used in calculation for this pass is also right-handed, with x' direction being the same as x direction, and y' and z' the reverse of y and z respectively. Therefore, the slow axis angles of both waveplates in x'y'z' are also the reverse of those in the xyz coordinate.

Both $E_x$ and $E_E$ fields have a phase shift of π upon reflection on a clear surface (unpatterned area) of the photomask. Effectively, the Jones matrix K of this reflection gives a phase shift of π only to Ey field:

$$K = \begin{bmatrix} 1 & 0 \\ 0 & -1 \end{bmatrix} \qquad \text{Equation 8}$$

When the illumination light travels along z' direction, the product of the two Jones matrices of WP1 and WP2 is:

$$J_2(\delta_2, -\theta_2) \cdot J_1(\delta_1, -\theta_1)$$

The Jones vector before the PBS is:

$$E^{out} = J_1(\delta_1, \theta_1) \cdot J_2(\delta_2, \theta_2) \cdot K \cdot J_2(\delta_2, -\theta_2) \cdot J_1(\delta_1, -\theta_1) \cdot E^{in} \qquad \text{Equation 9}$$

The y component intensity is:

$$|E_y^{out}|^2 = E_1^2 [\sin(\beta)\cos(\alpha)(A_0^2 - A_1^2 + A_2^2 - A_3^2) + 2\sin(\beta)\sin(\alpha)(A_0 A_1 + A_2 A_3)]^2 + E_1^2 [-2\sin(\beta)\cos(\alpha)(A_0 A_1 + A_2 A_3) + 2\cos(\beta)(A_1 A_2 - A_0 A_3) + \sin(\beta)\sin(\alpha)(A_0^2 - A_1^2 + A_2^2 - A_3^2)]^2$$

Equation 10

The definitions of $A_o$, $A_1$, $A_2$, and $A_3$ are the same as in TL case. The light intensity captured by the sensor is:

$$F = \in \cdot E_1^2 + (1-\in)|E_y^{out}|^2 \qquad \text{Equation 11}$$

In an RL polarization measurement for the illustrated system 100, the incident illumination light is always at x-polarization. One only needs to take measurements for WP1(λ/4) rotation since this data is sufficient to determine the retardance and orientation of both waveplates from one single nonlinear fit, from which the polarization state on the mask plane may be calculated.

Figure 3:
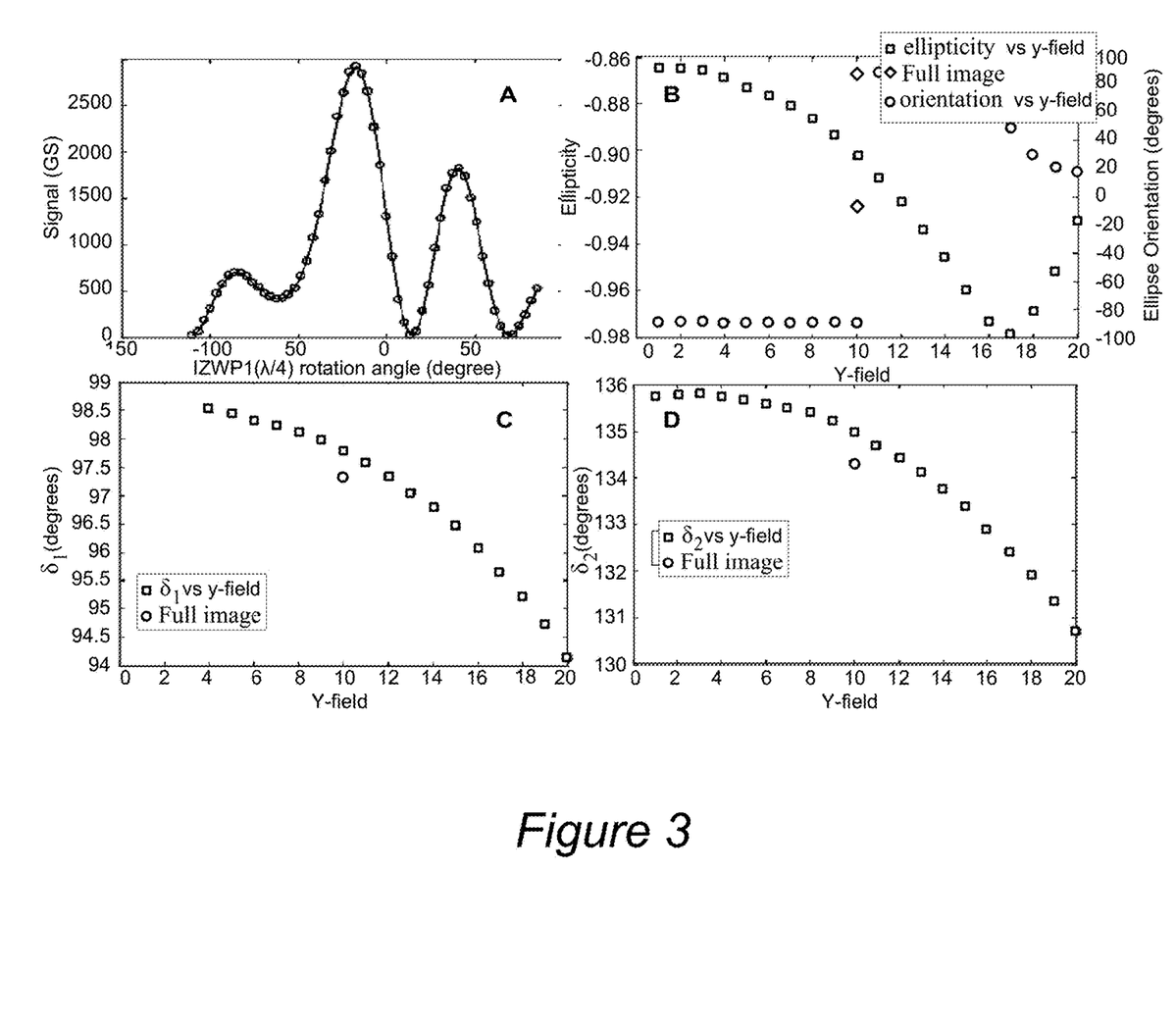
FIG. 3 shows one example of RL (reflected light) mode polarization measurement results from the same tool that is used for the TL mode results in accordance with one implementation of the present invention.

FIG. 3 shows one example of RL polarization measurement results after nonlinear least squares fitting data processing from the same tool that is used for the TL mode results. In one implementation, the captured or detected images may be divided into 20 slices along the y-field so as to measure the y-field dependence of the polarization state on the mask plane. The images may be divided into any suitable number of slices. For instance, the number of slices may be between 10 and 40.

In the example measurements obtained from the 6xx tool from KLA-Tencor, the determined retardance parameters $\delta_1$ and $\delta_2$ for the RL mode are significantly different from those for the TL mode measurements. This difference is likely caused by system errors, especially objective residual birefringence since the light passes twice through the objective for the RL mode. In fact, there may be challenges in modelling the data of a WP2(3λ/8) rotation because of the existence of residual birefringence ($\delta_{obj}$) of the objective.

The objective (including all optics between mask and WP2) residual birefringence was determined to be a few degrees, which is much smaller than the retardance $\delta_2$. In the RL polarization measurements, the effect of $\delta_{obj}$ can be included in an effective $\delta_2'$, e.g., objective and WP2 can be approximated by one effective waveplate. This assumption is based on the equivalence theorem in Jones calculus, which states that an optical system consisting of a sequence of retarders is equivalent to a single retarder followed by a rotation matrix. For the problem being solved, the rotation matrix has been determined to be very close to an identity matrix and can be ignored.

For the two-retarder case of objective and WP2, the effective retardance $\delta_2'$ is a sinusoidal function of the relative orientation angle between the objective and WP2:

$$\delta_2' = \delta_2 + \delta_{obj} \cdot \sin(2\phi + \tau)$$

$\phi$ is the relative angle (between objective and WP2) and $\tau$ is a phase. The factor of 2 in the above equation comes from the fact that the effect of a waveplate is the same if it is rotated by 180°. For the RL polarization measurements, the fitted retardance of WP2 is determined to be $\delta_2'$. If one performs RL polarization measurements (i.e., by rotating WP1(λ/4) and recording light intensity) for multiple WP2 (3λ/8) positions, this sinusoidal behavior of $\delta_2'$ can be observed and the true $\delta_2$ and $\delta_{obj}$ values can be determined directly, using the above equation for $\delta_2'$.

Figure 4:
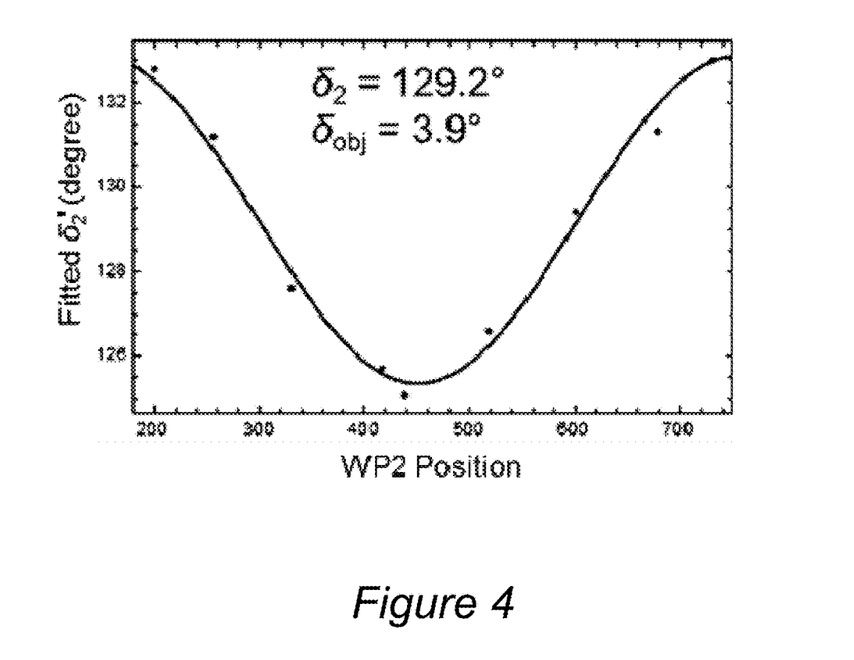
FIG. 4 displays one example of the fitted effective waveplate retardance vs. orientation positions (in motor counts) in accordance with one implementation of the present invention.

FIG. 4 displays one example of the fitted $\delta_2'$ vs. WP2 orientation positions (in motor counts), which clearly shows a sinusoidal dependence. Converting the motor counts into radians, one may determine $\delta_{obj}$ and $\delta_2$ from the sinusoidal fit of FIG. 4. In this example, $\delta_{obj}$ is 3.9° and $\delta_2$ is 129.2°. If more than one detection plane is being used, the results may be averaged. In the 6xx tool, which has two detection planes P0 and P1, the results from the P0 and P1 (not shown here) detection planes may be averaged together, e.g., resulting in a $\delta_{obj}$ of 3.6°.

Figure 5:
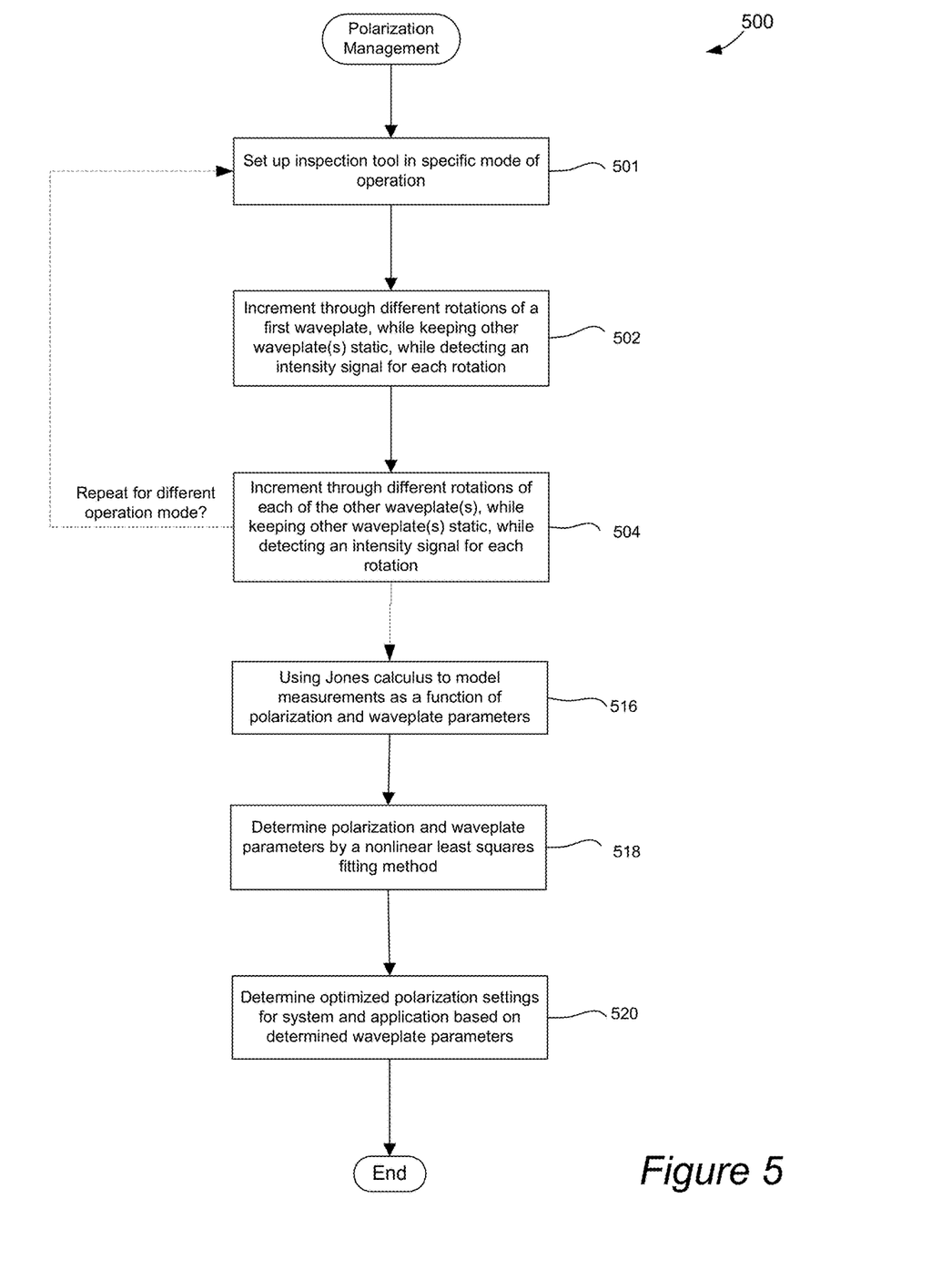
FIG. 5 is a flow chart illustrating a procedure for managing polarization in accordance with one embodiment of the present invention.

Any suitable technique may be used to obtain and utilize various polarization parameters in an inspection system. FIG. 5 is a flow chart illustrating a procedure 100 for managing polarization in accordance with one embodiment of the present invention. Initially, the inspection tool may be set up in a specific mode of operation in operation 501. For example, a TL or RL mode may be selected.

The process 500 may then include incrementing through different rotations for a first waveplate, while keeping other one or more waveplate(s) static in operation 502. Additionally, an intensity signal may also be detected at each rotation. For instance, images may be collected at each rotation. After a first waveplate is rotated, each of the other two or more waveplates may then be incrementally rotated, while an intensity signal is collected for each rotation, in operation 504, e.g., from the unpatterned areas of the photomask. If there are two waveplates as illustrated in the system of FIG. 1, the first waveplate and then the second waveplate are rotated while the other waveplate remains static. If there are more than two waveplates, then each of the other waveplates (e.g., 3$^{rd}$ waveplate, 4$^{th}$ waveplate, etc.) are then rotated one at a time while the other waveplates are kept static.

The entire set of waveplates may each be incrementally rotated one at a time under the particular mode of operation. This process may then be repeated for each waveplate under a next mode of operation. For example, each waveplate is incrementally rotated under the TL mode and then under the RL mode. Intensity values are collected for each set of rotations for each waveplate and each operation mode.

Referring back to the illustrated process 500, the measurements may then be modelled using Jones calculus as a function of the polarization parameters and waveplate parameters in operation 516. The polarization and waveplate parameters may also be determined based on a nonlinear least squares fitting method in operation 518. For instance, the polarization parameters and the waveplate retardance and orientation parameters can be determined using equations 4 and 5. In a specific implementation, a least squares fit process, such as the Levenberg-Marquardt algorithm (LMA), may be used. Other nonlinear fitting algorithms (such as the Gauss-Newton algorithm, QR decomposition, gradient methods, direct search methods, etc.) may alternatively or additionally be used. Details of LMA can be easily found in references such as the book publication "Numerical Recipes: The Art of Scientific Computing" by William H. Press et al. Below, a brief summary of this algorithm is included.

Assuming one has a set of n data points $(x_i, y_i)$, which are fitted to a physical model of m parameters $F(x, p_1, p_2, \ldots, p_m)$. The index i runs from 1 to n. In this patent application, the symbol x stands for waveplate rotation angle and y stands for the signal measured by the sensor. The fitted parameters include both polarization and waveplate parameters. All the parameters are determined when the Chi-square value reaches a minimum.

$$\chi^2 = \Sigma_{i=1}^{n}(y_i - F_i)^2 \qquad \text{Equation 12}$$

$F_i$ is the model value with $x = x_i$ and a set of parameter values. In order to find a solution of all parameters from the set of n data points $(x_i, y_i)$, an iteration process is typically used because for such a complex problem, there is no analytical solution for the parameters. The Jacobian matrix M has a size of n×m. The ij$^{th}$ element of this matrix is $$M_{ij} = \frac{\partial F(x_i)}{\partial p_j} \qquad \text{Equation 13}$$

The index j runs from 1 to m. The Jacobian matrix is calculated by taking the partial derivatives of model F with respect to all fitted parameters. For the method developed in this application, the Jacobian matrix can be written down analytically. The curvature matrix size is m×m. It is defined as $$C = M^\dagger M + \lambda \cdot \text{diag}(M^\dagger M) \qquad \text{Equation 14}$$

$\lambda$ is called damping factor. It starts with an initial value and is adjusted, depending on the Chi-square value, after each iteration. Its purpose is to make the nonlinear least squares fitting process numerically stable. For each iteration cycle, the discrepancy between the data and model prediction is $$\delta y = M^\dagger (y - F) \qquad \text{Equation 15}$$

For each iteration cycle, the correction to the parameter vector $(p_1, p_2, \ldots, p_m)$ is found by solving the following matrix equation $$C \cdot \delta p = \delta y \qquad \text{Equation 16}$$

The calculated parameter correction is added to the parameter vector after each iteration cycle and the new parameter vector will be used for next iteration. This process stops when the parameter correction is smaller than a preset threshold, at which the iteration process is defined as converged. In order to make the above LMA succeed, one has to start the iteration process with a set of initial values of fitted parameters, which are close to the converged solution values and can be estimated from the physical conditions of the problem to be solved.

In the example of FIG. 1, only the WP1($\lambda/4$) 104b is first rotated stepwise through a range about 180°, while the WP2 ($3\lambda/8$) remains static in the TL mode. The intensity measurements that were obtained for the different WP1 rotations may then be used to determine its retardance $\delta_1$, slow axis angle $\theta_1$, and the polarization state between WP1 and WP2, by way of example. With WP1($\lambda/4$) set to a fixed $\theta_1$ angle and rotating WP2($3\lambda/8$) in a stepwise fashion through a range of 180° and taking the retardance parameters $\delta_1$ and $\theta_1$ from the first waveplate measurements, the polarization state between WP2 and objective, retardance $\delta_2$ and slow axis angle $\theta_2$ may also be determined from the above modelling equation for the TL mode (Equation 4 and 5). The slow axis angles $\theta_1$ and $\theta_2$ correspond to the known static rotation settings of the corresponding waveplates WP1 and WP2, respectively. If the objective does not cause any polarization state change, then the polarization state on the mask plane may also be determined.

In the RL mode measurement example of FIG. 1, the incident illumination light is always at x-polarization. Rotation of the WP1($\lambda/4$) waveplate is sufficient to determine the retardance and orientation of both waveplates from one single nonlinear fit, from which the polarization state on the mask plane may then be easily calculated.

One may utilize the determined polarization and waveplate parameters in any suitable application. As shown in FIG. 5, optimized polarization settings may be determined based on the determined waveplate parameters in operation 520. For example, the determined $\delta_1$, $\delta_2$, and $\delta_{obj}$ parameters may be used to simulate arbitrary polarization states for a plurality of waveplate rotations. For instance, rotation of WP1($\lambda/4$) and WP2($3\lambda/8$) may be modeled to generate arbitrary polarization states on the mask plane in RL mode.

Figure 6A:
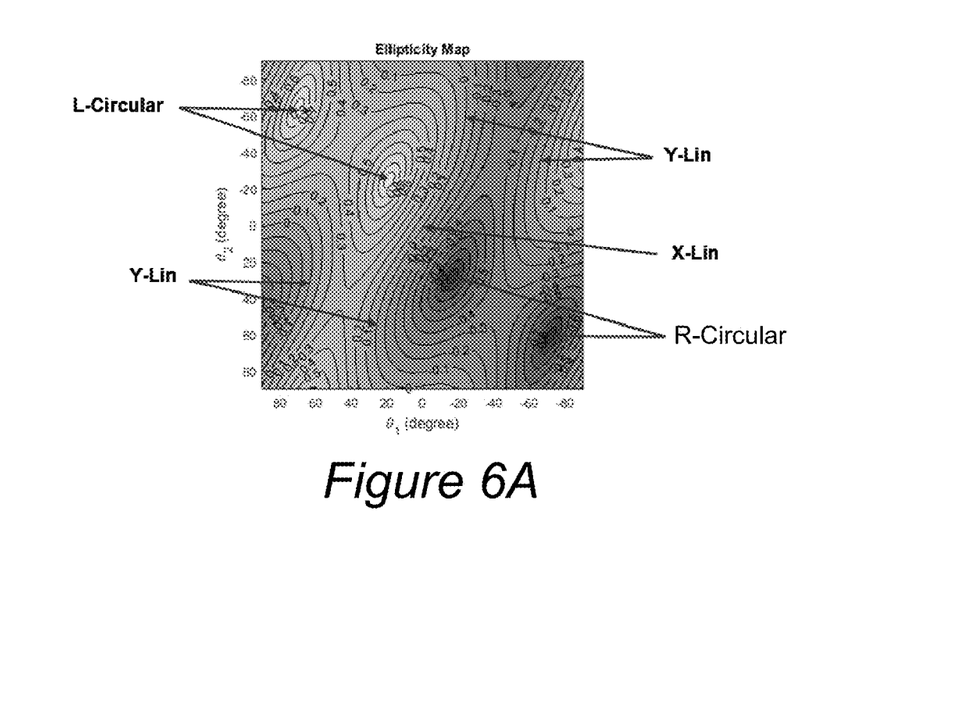
FIGS. 6A and 6B show simulated maps of ellipticity and ellipse orientation angle, respectively, on the mask plane when both waveplates are rotated within a range of 180°, with typical values for waveplate and objective retardance, in accordance with one embodiment of the present invention.
Figure 6B:
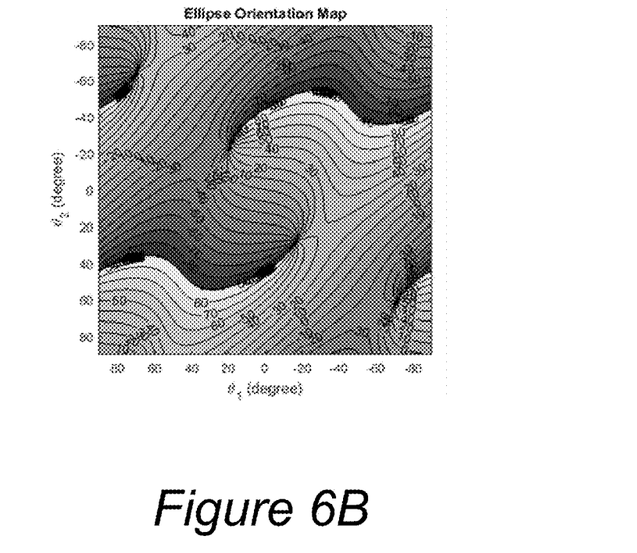

FIGS. 6A and 6B show simulated maps of ellipticity and ellipse orientation angle, respectively, on the mask plane when both waveplates are rotated within a range of 180°, with typical values of $\delta_1$, $\delta_2$, and $\delta_{obj}$ in RL mode. Specifically, FIG. 6A illustrates a simulated ellipticity map, and FIG. 6B illustrates an ellipse orientation angle map. The maps include simulated, arbitrary polarization states from left- to right-circular polarization. The waveplate setting angles of certain important polarization states are labelled on the maps. For instance, Y-linear ellipticity is shown on 0 value contour lines with corresponding points on the ellipse orientation map having +/−90° orientation angle, while an X-linear ellipticity is also shown on 0 value contour lines but with zero degree orientation angle on the ellipse orientation map. Right- and left-handed circular ellipticity are located at −1 and +1 value contour positions, respectively.

One specific capability of polarization state control is to rotate the orientation angle of linear polarization from −90° to 90° by tuning the rotations of the waveplates to result in a polarization state along the zero contour lines of the ellipticity map in FIG. 6A and a certain orientation in FIG. 6B. That is, waveplate orientation angles that result in an arbitrary polarization state at the sample can be obtained from the simulated ellipticity and ellipse orientation maps of FIGS. 6A and 6B. Being able to achieve linear polarization is especially relevant to EUV photomask inspection because the signal strength that is detected from certain types of defect strongly depends on the linear polarization orientation of illumination light.

Figure 7A:
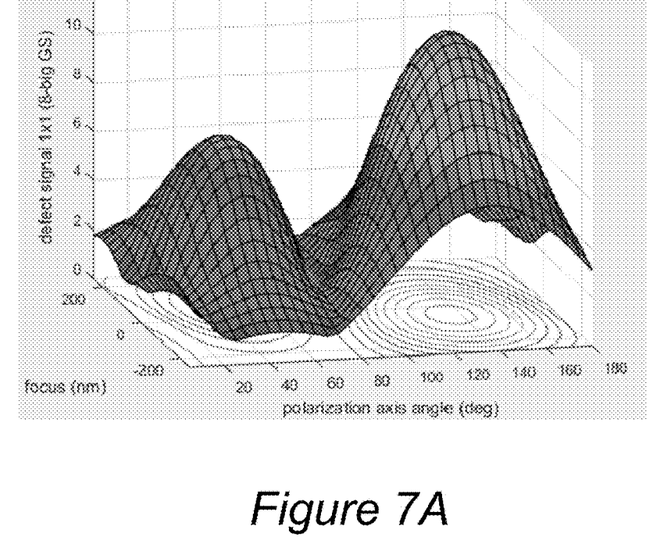
FIGS. 7A and 7B show both simulation and experimental verification results of a particular category of defect on an EUV (extreme ultra-violet) mask as a function of orientation angle and focus in accordance with one embodiment of the present invention.
Figure 7B:
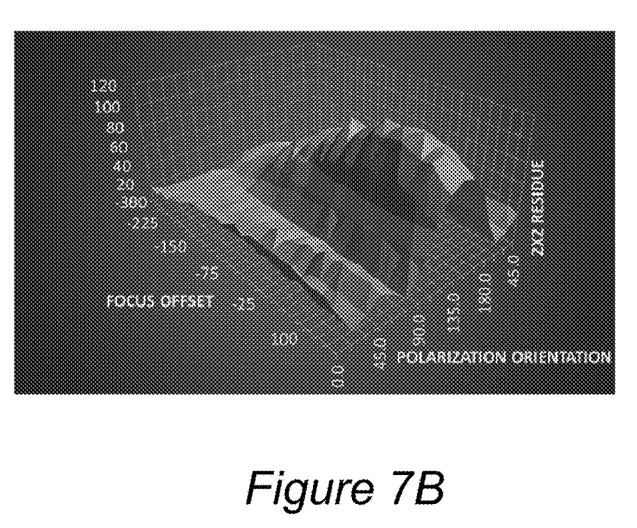

To give one example application, FIGS. 7A and 7B show both PROLITH simulation and experimental verification results of a particular category of defect on an EUV mask as a function of orientation angle and focus in accordance with one embodiment of the present invention. When the orientation angle of the linear polarization illumination light is rotated from 0° to 180°, it is equivalent to rotating from −90° to 90°. FIG. 7A shows simulation results, while FIG. 7B shows experimental results. As shown in both plots, the defect signal has a very strong dependence with the orientation angle. Near 15° and 75° angles, for example, the signal is near the minimum. In contrast near 45° and 135°, the defect signal peaks and is enhanced multiple times as compared to the minimum signal. The orientation angles that result in a maximized signal for a particular defect type can then be selected. The asymmetry between 45° and 135° signal peaks is expected.

Figure 8:
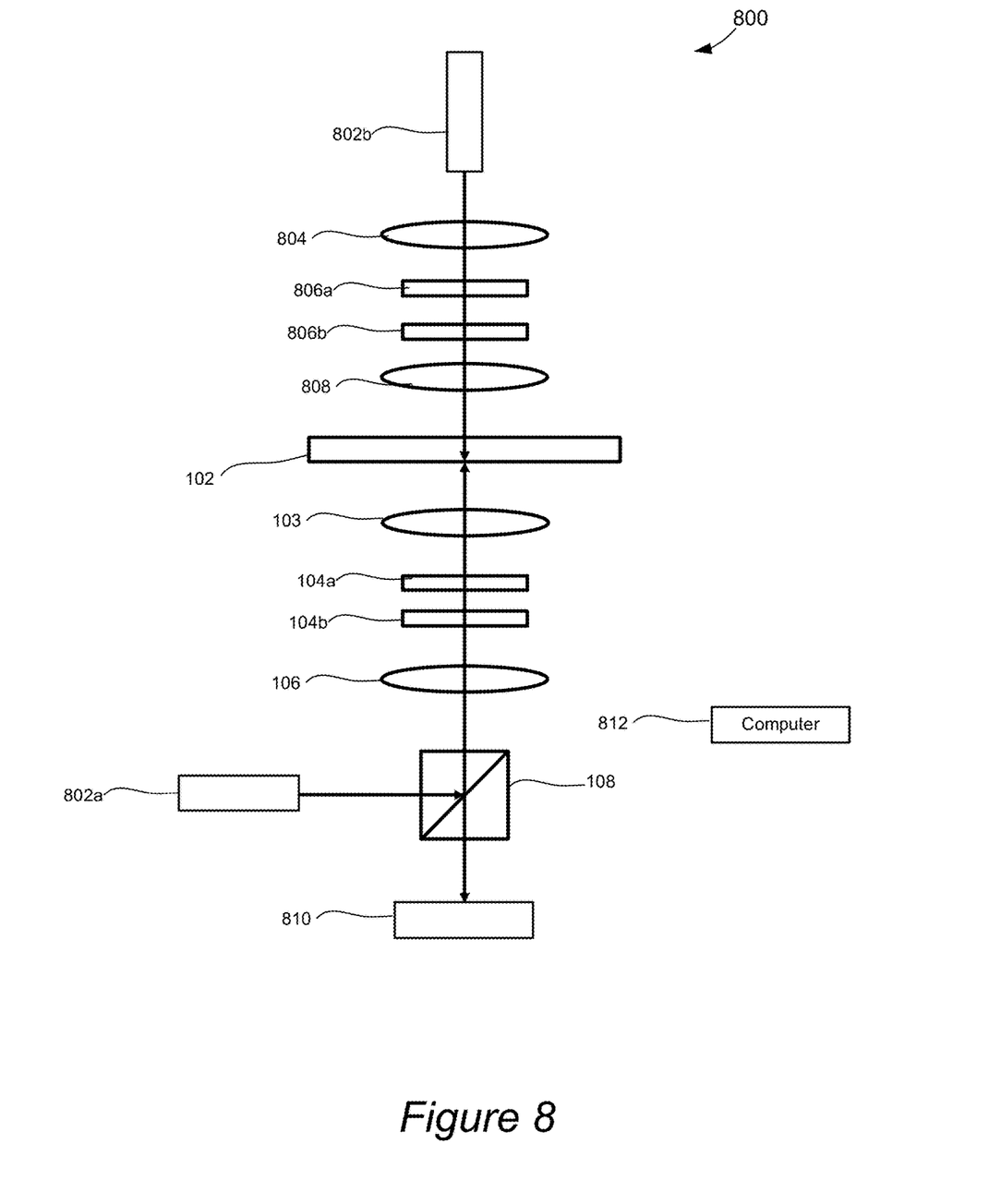
FIG. 8 is a diagrammatic representation of a system, which includes both TL and RL side waveplates, in accordance with one embodiment of the present invention.

The TL polarization state can similarly be controlled by a cascade of multiple waveplates to generate arbitrary polarization state on the mask plane. FIG. 8 is a diagrammatic representation of a system 800, which includes TL side waveplates, in accordance with one embodiment of the present invention. As shown, the system 800 includes a TL light source 802*b* for generating an illumination beam, a relay lens 804 for relaying the illumination beam, a first waveplate 806*a*, a second waveplate 806*b*, and a condenser lens 808 for focusing the illumination beam towards the sample 102. In addition to the RL illumination source 802*a* and sensor 810, the other components of RL side of the system 800 may be similar to the components of FIG. 1.

Examples of light sources for generating the RL or TL incident beam (e.g., any suitable electromagnetic waveform) include a laser-driven light source, a high-power plasma light source, a transillumination light source (e.g., halogen or Xe lamp), a filtered lamp, LED light sources, etc. The inspection system may include any suitable number and type of additional light sources, including broadband light sources.

The incident TL and/or RL beam from the light source may generally pass through any number and type of lenses which serve to relay (e.g., shape, focus or adjust focus offset, filter/select wavelengths, filter/select polarization states, resize, magnify, reduce distortion, etc.) the beam towards a sample. For instance, the illumination module for both the TL and RL paths may also include any number of linear polarizers and waveplates as described further herein.

The collection module of the system 800 may include any suitable number and type of optical components (not shown), such as an aperture or field stop, collimator, aperture mask, analyzer subsystem, splitter, and focus lens for focusing the scattered light towards a sensor 810. A magnified image of the sample is formed on the image sensor at back end of collection path. By way of example, the sensor 810 may be in the form of a CCD (charge coupled device) or TDI (time delay integration) detector, photomultiplier tube (PMT), or other sensor.

Similar to the RL mode, arbitrary TL polarization state can also be generated on the photomask plane, e.g., by using a pair of waveplates λ/4 and 3λ/8. One difference between TL and RL is that the photomask substrate can have significantly residual birefringence, which changes the TL polarization state when it transmits through the substrate. Therefore, in order to precisely control the TL polarization state on the mask plane, one either uses a photomask substrate of very low birefringence or uses a photomask substrate with its residual birefringence measured accurately in advance. The effect of substrate birefringence may then be compensated by the multiple waveplates used for TL polarization control. In order to realize target TL polarization state (e.g. linear or circular) on the bottom surface of the photomask substrate (102 in FIG. 8), the TL polarization state on the top surface of the substrate is generally a certain elliptical polarization state because of residual birefringence of the substrate. Based on FIGS. 6A and 6B, TL side multiple waveplates can generate arbitrary polarization states, including the above elliptical polarization state on the top surface of the photomask.

Certain embodiments described above allow arbitrary polarization state measurements and control for photomask inspection, especially for EUV photomask inspection. Under different inspection and specimen conditions, a specific polarization angle can be selected to minimize noise and improve defect SNR and, thereby, improve defect detection sensitivity. These techniques can provide a convenient and accurate solution to the challenge of illumination light polarization measurement and control. Certain techniques can serve to both expand and consolidate the capability of inspection tools. For example, next generation EUV scanners will have anamorphic designs, resulting in circular contacts on the wafer and requiring rectangular instead of square contact arrays on the reticle. The rectangular contact arrays will demand linear polarization orientation at an angle different from 0, 45, 90, or 135 degrees in order to optimize SNR (signal to noise ratio) for certain defect types.

Any suitable tool may be utilized, as long as variable polarization states may be set up on the tool. In general, an applicable inspection tool for implementation of techniques of the present invention may include at least one light source for generating an incident light beam at different polarization states. Such an inspection may also include illumination optics for directing the incident beam to the area-of-interest, collection optics for directing scattered electromagnetic waveforms (e.g., scattered light, X-rays, etc.) from the area-of-interest in response to the incident beam, a sensor for detecting this scattered output and generating an image or signal from the detected scattered output, and a controller or computer subsystem for controlling the components of the inspection tool and facilitating polarization control and defect detection in various materials and structures as described further herein.

Regardless of form, a computer subsystem (e.g., 812) may be connected to both illumination subsystem and analyzer subsystem for automated control. For instance, the signals captured by each detector can be processed by computer subsystem, which may include a signal processing device having an analog-to-digital converter configured to convert analog signals from each sensor into digital signals for processing. The computer subsystem may be configured to analyze intensity, phase, and/or other characteristics of the sensed light beam. The computer subsystem may be configured (e.g., with programming instructions) to provide a user interface (e.g., on a computer screen) for displaying resultant images and other inspection characteristics. The computer subsystem may also include one or more input devices (e.g., a keyboard, mouse, joystick) for providing user input (e.g., as changing wavelength, polarization, mask configuration, aperture configuration, etc.), viewing detection results data or images, setting up an inspection tool recipe, etc.

The computer subsystem may be any suitable combination of software and hardware and is generally configured to control various components or other controllers of the inspection system. The computer subsystem may control selective activation of the illumination source, the illumination or output aperture settings, wavelength band, focus offset setting, polarization settings, analyzer settings, etc. The computer subsystem 624 may also be configured to receive images or signals generated by each detector and analyze the resulting images or signals to determine whether defects are present on the sample, characterize defects present on the sample, or otherwise characterize the sample. For example, the computer subsystem may include a processor, memory, and other computer peripherals that are programmed to implement instructions of the method embodiments of the present invention. The computer subsystem may also have one or more processors coupled to input/output ports, and one or more memories via appropriate buses or other communication mechanisms.

Because such information and program instructions may be implemented on a specially configured computer system, such a system includes program instructions/computer code for performing various operations described herein that can be stored on a computer readable media. Examples of machine-readable media include, but are not limited to, magnetic media such as hard disks, floppy disks, and magnetic tape; optical media such as CD-ROM disks; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

Regardless of the particular system embodiment, each optical element may be optimized for the particular wavelength range of the light in the path of such optical element. Optimization may include minimizing wavelength-dependent aberrations, for example, by selection of glass type, arrangement, shapes, and coatings (e.g., anti-reflective coatings, highly reflective coatings) for minimizing aberrations for the corresponding wavelength range. For example, the lenses are arranged to minimize the effects caused by dispersion by shorter or longer wavelength ranges. In another embodiment, all the optical elements are reflective. Examples of reflective inspection systems and configurations are further described in U.S. Pat. No. 7,351,980 issued 1 Apr. 2008, which is incorporated herein by reference in its entirety.

The optical layout of the inspection tool can vary from that described above. For example, the system microscope objective lens can be one of many possible layouts, as long as the transmission coatings are optimized for the particular selected wavelength band or sub-band and the aberration over each waveband is minimized. Different light sources can be used for each path. For instance, a Xe source may be used for the long wavelength path and an HgXe or Hg lamp may be used for the short wavelength path. Multiple LED or speckle buster laser diodes are also possible sources for each path. The zoom ratio can be modified to include different magnification ranges either via a lens-only approach, a mostly fixed lens with an optical trombone, or any combination thereof.

As illustrated above, the sample may also be placed on a stage of the inspection system, and the inspection system may also include a positioning mechanism for moving the stage (and sample) relative to the incident beam. By way of examples, one or more motor mechanisms may each be formed from a screw drive and stepper motor, linear drive with feedback position, or band actuator and stepper motor. The one or more positioning mechanisms may also be configured to move other components of the inspection system, such as illumination or collection mirrors, apertures, FP relay lens, wavelength filters, polarizers, analyzers, waveplates, etc.

It should be noted that the above description and drawings of an inspection system are not to be construed as a limitation on the specific components of the system and that the system may be embodied in many other forms. For example, it is contemplated that the inspection or measurement tool may have any suitable features from any number of known imaging or metrology tools arranged for detecting defects and/or resolving the critical aspects of features of a reticle or wafer. By way of example, an inspection or measurement tool may be adapted for bright field imaging microscopy, dark field imaging microscopy, full sky imaging microscopy, phase contrast microscopy, polarization contrast microscopy, and coherence probe microscopy. It is also contemplated that single and multiple image methods may be used in order to capture images of the target. These methods include, for example, single grab, double grab, single grab coherence probe microscopy (CPM) and double grab CPM methods. Non-imaging optical methods, such as scatterometry, may also be contemplated as forming part of the inspection or metrology apparatus.

Any suitable lens arrangement may be used to direct the incident beam towards the sample and direct the output beam emanating from the sample towards a detector. The illumination and collection optical elements of the system may be reflective or transmissive. The output beam may be reflected or scattered from the sample or transmitted through the sample. Likewise, any suitable detector type or number of detection elements may be used to receive the output beam and provide an image or a signal based on the characteristics (e.g., intensity) of the received output beam.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. For example, the defect detection characteristic data may be obtained from a transmitted, reflected, or a combination output beam. Accordingly, the present embodiments are to be considered as illustrative and not restrictive, and the invention is not to be limited to the details given herein.

What is claimed is:

1. A system for controlling and measuring polarization for inspection of a sample, comprising:
   an illumination optics subsystem for generating and directing illumination light towards a sample, wherein the illumination optics subsystem includes two or more illumination polarization components for controlling the polarization state of the illumination light;
   a collection optics subsystem for collecting output light from non-patterned areas of the sample in response to the illumination light, wherein the collection optics subsystem comprises at least a first and second collection polarization component for measuring polarization state of the illumination light at or near the sample and a sensor for detecting the output light after the polarization state is adjusted by the first and second collection polarization components; and
   a controller that is configured to perform the following operations:

setting up the system in a specific mode of operation;
incrementing the first collection polarization component through a plurality of rotations while keeping the second collection polarization component static;
measuring an intensity signal by the sensor for each rotation of the first collection polarization component;
incrementing the second collection polarization component through a plurality of rotations while keeping the first collection polarization component static;
measuring an intensity signal by the sensor for each rotation of the second collection polarization component;
generating a model of a plurality of polarization state and polarization component parameters for the system to simulate the intensity signals that were measured for each rotation of the first and/or second collection polarization component; and
determining the polarization state and polarization component parameters for the system based on the model.

2. The system of claim 1, wherein:
the sample is a photomask,
the illumination optics subsystem includes one or more light sources for generating illumination light that is transmitted through the sample in a transmitted light (TL) mode,
the at least first and second collection polarization components comprise a first and second waveplate,
the system is set up in the TL mode,
a model is first generated based on Jones calculus and used to determine a retardance value for the first waveplate and the polarization state between the first waveplate and the second waveplate based on measuring for each rotation of such first waveplate, and
a model is next used to determine a retardance of the second waveplate and the polarization state at or near the sample based on measuring for each rotation of such second waveplate and the determined retardance of the first waveplate and its static rotation position.

3. The system of claim 2, wherein the first waveplate is a rotatable ¼ waveplate and the second waveplate is a rotatable ⅜ waveplate, wherein the ⅜ waveplate is positioned to receive the output light from the sample, after which the ¼ waveplate receives the output light from the ⅜ waveplate.

4. The system of claim 3, wherein the illumination optics subsystem includes one or more light sources for generating illumination light that is reflected from the sample in a reflected light (RL) mode, wherein the collection optics subsystem includes a polarizing beam splitter (PBS) for receiving the output light from the ¼ waveplate and transmitting only a y-polarization component of the output light towards the sensor, wherein the PBS is arranged and configured to reflect only an x-polarization component of illumination light in a reflecting light (RL) mode towards the sample.

5. The system of claim 4, wherein the polarization state of the illumination light at or near the sample is determined as a function of field position.

6. The system of claim 4, wherein the first and second waveplates are the same as at least some of the illumination polarization components, and wherein the controller is further configured for performing the following operations:
setting up the system in RL mode;
in the RL mode, incrementing the first waveplate through a plurality of rotations while keeping the second waveplate static;
in the RL mode, measuring an intensity signal by the sensor for each rotation of the first waveplate;
in the RL mode, generating a model based on Jones calculus and of a plurality of polarization and waveplate parameters, including the retardance of the first and second waveplates, for the system to simulate the intensity signals that were measured in the RL mode for each rotation of the first waveplate; and
in the RL mode, determining illumination polarization state at or near the sample based on the retardance of the first and second waveplates that was determined in the RL mode and based on the rotation of the first waveplate.

7. The system of claim 6, wherein the controller is further configured for, in the RL mode, modeling a sinusoidal behavior of the retardance of the second waveplate as a function of rotation and separating a real retardance of the second waveplate from a retardance of an objective of the system based on such modelled sinusoidal behavior.

8. The system of claim 1, wherein the at least first and second collection polarization component comprise a plurality of waveplates having a retardance sum equal to or greater than a half wave.

9. The system of claim 1, wherein the collection optics subsystem includes multiple detection planes for detecting output light, and the controller is further configured to model and determine the polarization state and polarization component parameters for measurements at the multiple detection planes and average the determined polarization state and polarization component parameters from such multiple detection planes.

10. The system of claim 1, wherein the model is based on Jones calculus and uses a nonlinear least squares fit process to determine the polarization state and polarization component parameters.

11. The system of claim 1, wherein the controller is further configured for simulating a plurality of polarization states at or near the sample based on the determined polarization state and polarization component parameters and selecting a rotation for the first and second collection polarization components to result in a particular orientation of linear polarization at the sample.

12. A method of controlling and measuring polarization for inspection of a sample, comprising
setting up an inspection system in a specific mode of operation;
incrementing a first polarization component of the system through a plurality of rotations while keeping a second polarization component of the system static;
measuring an intensity signal from non-patterned areas of the sample for each rotation of the first polarization component;
incrementing the second polarization component through a plurality of rotations while keeping the first polarization component static;
measuring an intensity signal from non-patterned areas of the sample for each rotation of the second polarization component;
generating a model of a plurality of polarization state and polarization component parameters for the system to simulate the intensity signals that were measured for each rotation of the first and/or second polarization component; and
determining the polarization state and polarization component parameters for the system based on the model.

13. The method of claim 12, wherein:
the system is set up in a transmitted light (TL) mode,
the first and second polarization components are a first and second waveplate,
the sample is a photomask,
a model is first generated and used to determine a retardance value for the first waveplate and the polarization state between the first and second waveplate based on measuring for each rotation of such first waveplate, and
a model is next used to determine a retardance of the second waveplate and the illumination polarization state at or near the sample based on measuring for each rotation of such second waveplate and the determined retardance of the first waveplate and its static rotation position.

14. The method of claim 13, wherein the first waveplate is a rotatable ¼ waveplate and the second waveplate is a rotatable ⅜ waveplate, wherein the ⅜ waveplate is positioned to receive the output light from the sample, after which the ¼ waveplate receives the output light from the ⅜ waveplate.

15. The method of claim 14, wherein only a y polarization component of the output light is measured, wherein only an x polarization component of illumination light in RL mode towards the sample.

16. The method of claim 15, wherein the illumination polarization state at or near the sample is determined as a function of field position.

17. The method of claim 15, further comprising:
setting up the system in RL mode;
in the RL mode, incrementing the first waveplate through a plurality of rotations while keeping the second waveplate static;
in the RL mode, measuring an intensity signal for each rotation of the first waveplate;
in the RL mode, generating a model of a plurality of polarization state and waveplate parameters, including the retardance of the first and second waveplates, based on Jones calculus to simulate the intensity signals that were measured in the RL mode for each rotation of the first waveplate; and
in the RL mode, determining illumination polarization state at or near the sample based on the retardance of the first and second waveplates that was determined in the RL mode and based on the rotation of the first waveplate.

18. The method of claim 17, further comprising, in the RL mode, modeling a sinusoidal behavior of the retardance of the second waveplate as a function of rotation and separating a real retardance of the second waveplate from a retardance of an objective of the system based on such modelled sinusoidal behavior.

19. The method of claim 12, wherein the model is based on Jones calculus and uses a nonlinear least squares fit process to determine the polarization state and polarization component parameters.

20. The method of claim 12, further comprising simulating a plurality of polarization states at or near the sample based on the determined polarization state and polarization component parameters and selecting a rotation for the first and second collection polarization components to result in a particular orientation of linear polarization at the sample.

* * * * *

UNITED STATES PATENT AND TRADEMARK OFFICE
CERTIFICATE OF CORRECTION

PATENT NO. : 10,168,273 B1
APPLICATION NO. : 15/795089
DATED : January 1, 2019
INVENTOR(S) : Huang et al.

Page 1 of 1

It is certified that error appears in the above-identified patent and that said Letters Patent is hereby corrected as shown below:

In the Claims

Column 19, Claim 15, Line 3: change "illumination light in RL mode" to -- illumination light is reflected in RL mode --.

Column 20, Claim 17, Line 9: change "polarization state" to -- polarization --.

Signed and Sealed this
Nineteenth Day of February, 2019

Andrei Iancu
*Director of the United States Patent and Trademark Office*